US00PP27639P3

(12) United States Plant Patent
Danziger

(10) Patent No.: US PP27,639 P3
(45) Date of Patent: Jan. 31, 2017

(54) ***HEUCHERA* PLANT NAMED 'DKIRA95'**

(50) Latin Name: *Heuchera*
Varietal Denomination: DKIRA95

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 101 days.

(21) Appl. No.: 14/120,856

(22) Filed: Jul. 3, 2014

(65) Prior Publication Data

US 2016/0007519 P1 Jan. 7, 2016

(51) Int. Cl.
*A01H 5/12* (2006.01)

(52) U.S. Cl.
USPC ..... Plt./440

(58) Field of Classification Search
USPC ..... Plt./440
See application file for complete search history.

*Primary Examiner* — Susan McCormick Ewoldt
(74) *Attorney, Agent, or Firm* — Cassandra Bright

(57) ABSTRACT

A new and distinct *Heuchera* cultivar named 'DKIRA95' is disclosed, characterized by a large leaf size, purple and greyed-purple foliage, mounded growth habit and full, strong plant structure. The new variety is a *Heuchera*, normally produced as an outdoor garden or container plant.

2 Drawing Sheets

Figure 1:
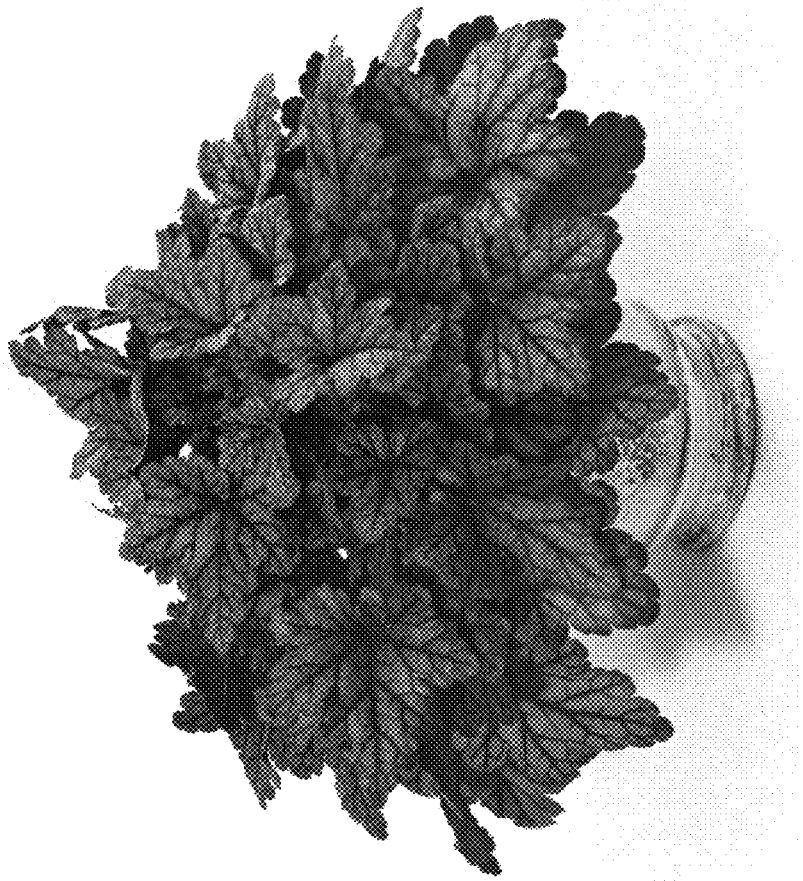

Latin name of the genus and species: *Heuchera*.
Variety denomination: 'DKIRA95'.

BACKGROUND OF THE INVENTION

The new *Heuchera* cultivar is a product of a planned breeding program conducted by the inventor, Gavriel Danziger, in Moshav Mishmar Hashiva, Israel. The objective of the breeding program was to produce new *Heuchera* varieties for ornamental commercial applications. The self pollination resulting in this new variety was made during January of 2009.

The parent is the unpatented, proprietary variety referred to as *Heuchera* 'HU-7-45', which was self-pollinated to produce seed, resulting in the new variety 'DKIRA95' The new variety was discovered in August of 2009 by the inventor in a group of seedlings resulting from the 2009 self-pollination, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in January of 2010 and has shown that the unique features of this cultivar are stable and reproduced true to type over many successive generations.

SUMMARY OF THE INVENTION

The cultivar 'DKIRA95' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DKIRA95' These characteristics in combination distinguish 'DKIRA95' as a new and distinct *Heuchera* cultivar:

1. Large leaf
2. Greyed-purple and purple leaf color.
3. Distinctive Purple and Greyed-Green vein coloration.
4. Mounded plant habit
5. Full and strong plant structure Plants of the new cultivar 'DKIRA95' are similar to plants of the parent, *Heuchera* 'HU-7-45' in most horticultural characteristics, however, plants of the new cultivar 'DKIRA95' differs in the following;

1. Smaller leaf size.
2. Fuller and stronger plant structure.
3. Petiole length is 6-8 cm. The parent petiole length is 12 cm.

COMMERCIAL COMPARISON

Plants of the new cultivar 'DKIRA95' are comparable to the unpatented, commercial variety *Heuchera* 'Palace Purple'. The two *Heuchera* varieties are similar in most horticultural characteristics; however, the new variety 'DKIRA95' differs in the following:

1. Dark Bronze leaf color of 'Palace Purple' compared to silver-green with purple rims of 'DKIRA95'.
2. Medium leaf size of 'Palace Purple' compared to large leaf size of 'DKIRA95'.
3. Spiny leaf margins of 'Palace Purple' compared to crenate leaf margin of "DKIRA95'.

Plants of the new cultivar 'DKIRA95' can also be comparable to the commercial variety *Heuchera* 'Caramel' U.S. Plant Pat. No. 16,560. The two *Heuchera* varieties are similar in most horticultural characteristics; however, the new variety 'DKIRA95' differs in the following:

1. Orange to pale yellow leaf color of 'Caramel' compared to Silver-Green with Purple rims of 'DKIRA95'.
2. Medium leaf size of 'Caramel' compared to large leaf size of 'DKIRA95'.

3. 'Caramel' is very sensitive to direct sunlight at the garden, whereas 'DKIRA95' can tolerate full sunlight.

BRIEF DESCRIPTION OF THE PHOTOGRAPHS

The accompanying photograph in FIG. 1 illustrates in full color a typical plant of 'DKIRA95' grown in a greenhouse, in a 12 cm pot. Age of the plant photographed is approximately 3 months from a rooted cutting.

Figure 2:
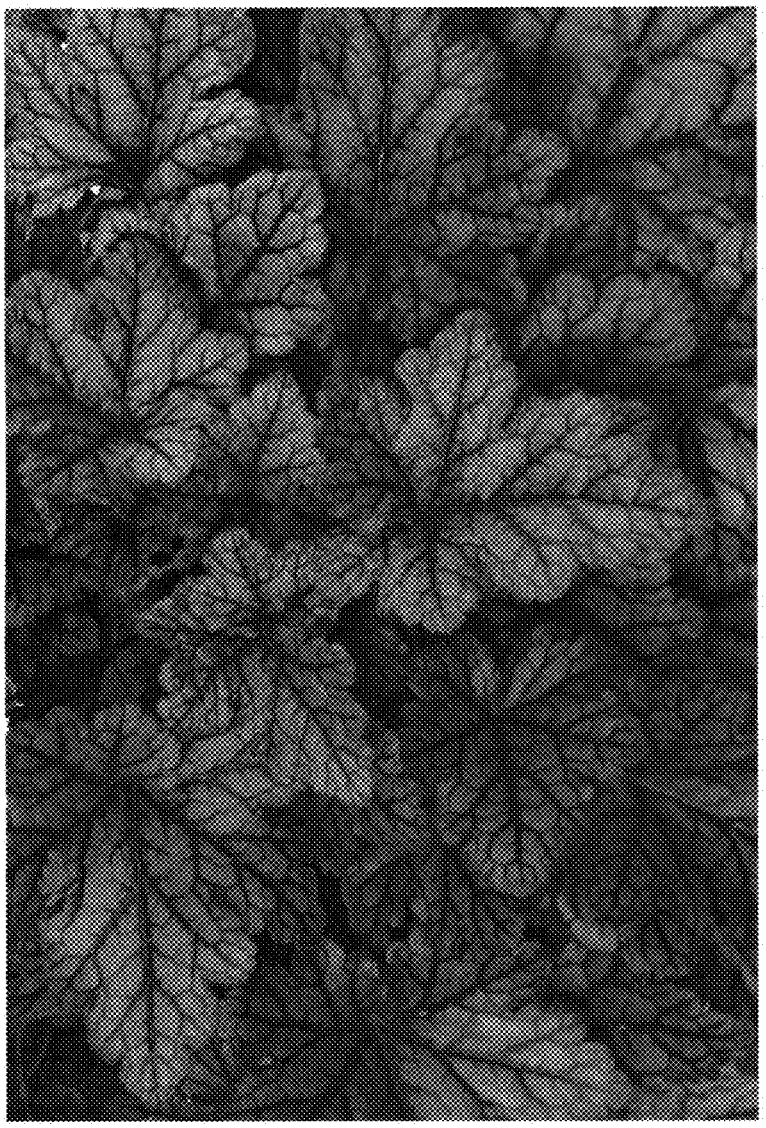

FIG. 2 illustrates a close up of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DKIRA95' plants grown in a greenhouse, in Moshav Mishmar Hashiva, Israel. The growing temperature ranged from 18° C. to 28° C. during the day and from 13° C. to 18° C. during the night. General light conditions are bright, normal sunlight. Measurements and numerical values represent averages of typical plant types.

Botanical classification: *Heuchera* 'DKIRA95'.

PROPAGATION

Type of propagation typically used: Cutting.

Time to initiate roots: About 12 days at approximately 25° C.

Root description: White, fleshy, fibrous.

Greenhouse production: Approximately 12-16 weeks from Transplanting in 12 cm pot (refers to growing inside the greenhouse, when rooted in early fall will bloom at mid winter or early spring for long period).

PLANT

Age of plant described: Approximately 12 weeks.

Container size of the plant described: 12 cm.

Growth habit: Mounded.

Height: Approximately 25-30 cm. to top of foliage.

Plant spread: Approximately 30 cm.

Growth rate: Moderate.

Branching characteristics: No lateral branches, foliage emerges from basal rosette.

FOLIAGE

Leaf:

*Arrangement*.—Rosette — Single.

*Compound or single*.—Single.

*Shape of blade*.—Overall narrow deltoid, with deep lobes.

*Average length*.—Approximately 12-14 cm.

*Average width*.—Approximately 12 cm.

*Apex*.—Broadly obtuse, lobed.

*Base*.—Cordate.

*Attachment*.—Petiolate.

*Margin*.—Crenate, gentle ciliate.

*Texture of top surface*.—Slightly rough (because of venation), slight pubescence.

*Texture of bottom surface*.—Slightly rough (because of venation).

*Leaf internode length*.—No internodes.

*Color*.—Marbled effect of dark green veins with silver-purple-red (younger leaves) or silver-green (mature leaves) interveinal areas. Young foliage upper side: Closest to Greyed-Purple N187B R.H.S. Young foliage under side: Closest to Greyed-Purple N186C R.H.S. Mature foliage upper side: Closest to Purple N77C R.H.S., margins near Greyed-Purple N186A. Mature foliage under side: Closest to Purple N77A R.H.S.

*Venation*.—Type: Reticulated. Venation color upper side: Young leaf — Near Purple N77A R.H.S. Mature leaf — Near Greyed-Green N189 R.H.S. Venation color under side: Young leaf — Near Red-purple 59A R.H.S. Mature leaf — Near Greyed-Purple group 187A. Durability of foliage to stresses: Good durability to full sun exposure, and drought.

Petiole:

*Average length*.—Approximately 6-8 cm.

*Diameter*.—Approximately 0.15-0.2 cm.

*Color*.—Near Approximately Red purple 64B.

*Strength*.—Strong, flexible, not easily breaking.

Other foliage characteristics: Slightly metallic. Color changes when leaf matures: when young, leaf is purple-red-silver and when mature, leaf is silver-green with purple rims.

FLOWER

*Flowering not observed to date.*

REPRODUCTIVE ORGANS

Reproductive organs not observed to date.

OTHER CHARACTERISTICS

Disease/pest resistance: Neither resistance nor susceptibility to normal diseases and pests of *Heuchera* have been observed.

Drought tolerance and cold tolerance: Hardy perennial USDA zone 4. Tolerates some drought without significant damage to plant.

What is claimed is:

1. A new and distinct cultivar of *Heuchera* plant named 'DKIRA95' as herein illustrated and described.

* * * * *